United States Patent [19]

Maine

[11] 4,196,355
[45] Apr. 1, 1980

[54] RADIATION SHIELD VEST AND SKIRT

[75] Inventor: Gayle J. Maine, Redmond, Oreg.

[73] Assignee: Shielding, Inc., Madras, Oreg.

[21] Appl. No.: 866,526

[22] Filed: Jan. 3, 1978

[51] Int. Cl.² ............................................. G21F 3/02
[52] U.S. Cl. ................................... 250/516; 250/519
[58] Field of Search .................. 2/2, 48; 250/516, 519

[56] References Cited

U.S. PATENT DOCUMENTS

| | | | |
|---|---|---|---|
| 2,344,811 | 3/1944 | Gill | 2/2 |
| 2,404,225 | 7/1946 | Green | 250/516 |
| 2,642,542 | 6/1953 | Weinberg | 250/516 |
| 3,991,420 | 11/1976 | Savarino | 2/2 |
| 3,996,620 | 12/1976 | Maine | 2/48 |
| 4,009,494 | 3/1977 | Nussbaum | 2/48 |

*Primary Examiner*—Harold A. Dixon
*Attorney, Agent, or Firm*—Kolisch, Hartwell, Dickinson & Stuart

[57] ABSTRACT

A two-piece radiation shield garment for the human body is disclosed comprising an adjustably overlapping vest to protect the upper body and a wraparound skirt to protect the lower body. The vest and skirt are constructed of multiple inner layers of flexible radiation shielding material covered with nonshielding fabric or other material. The vest and skirt may be attractively fashioned and decorated to encourage their use as a shield garment for women. The vest includes a rear shield panel joined to a pair of overlapping front shield panels. Similarly, the skirt includes a rear shield panel connected to a pair of overlapping front shield panels. The overlapping front panels of the vest and skirt have wide cooperating horizontal bands of Velcro-type tape closures providing an adjustable fit and a secure closure for the heavy materials. The vest and skirt overlap in the waist region when worn to provide continuous vertical and all-around protection to the body while allowing freedom of movement to the wearer.

9 Claims, 8 Drawing Figures

U.S. Patent    Apr. 1, 1980    4,196,355
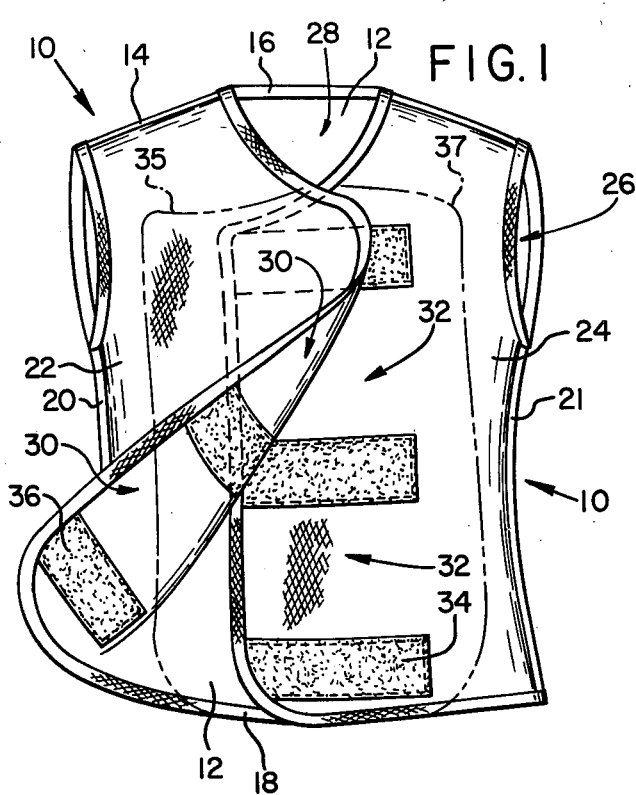
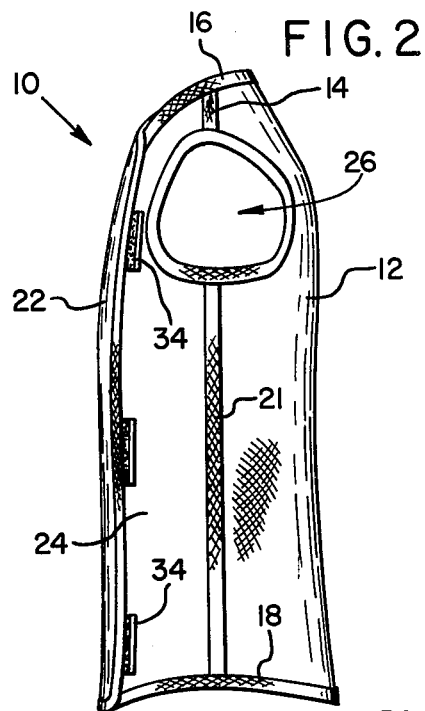
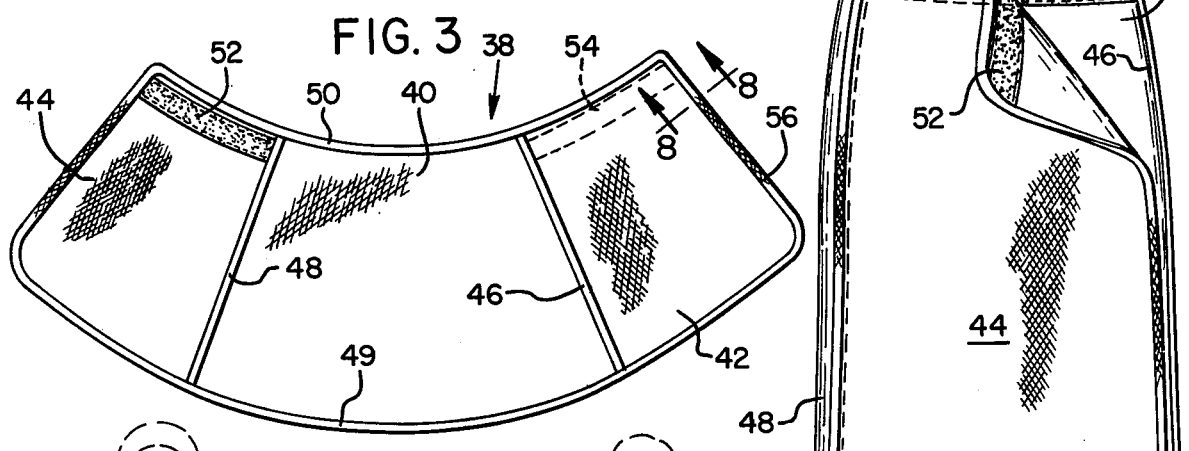
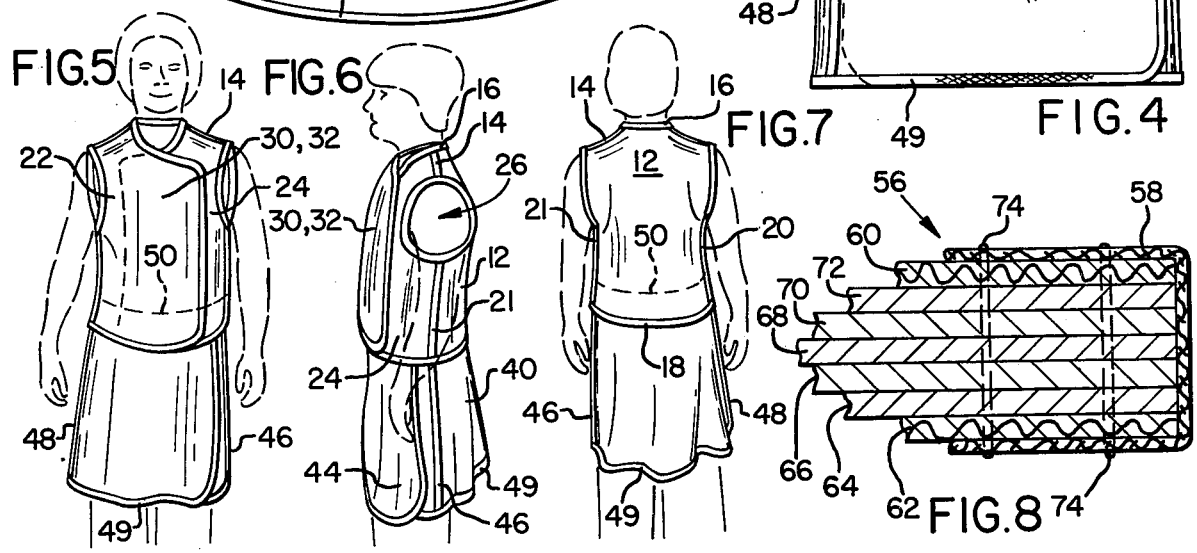

RADIATION SHIELD VEST AND SKIRT

BACKGROUND OF THE INVENTION

1. Field of the Invention

The present invention relates to a radiation shield garment for protecting the wearer from harmful X rays and other radiation.

2. Description of the Prior Art

Known radiation shield garments are commonly constructed as one-piece aprons. Such aprons are usually of two types. One type is used by patients who normally assume a sitting or prone position, while the other type, requiring means for securing the apron to the body, is used by doctors, dentists, X-ray technicians, and other workers who normally remain standing while near a radiation source. An example of the first type is shown in U.S. Pat. No. 3,093,829, and an example of the second type is illustrated in U.S. Pat. No. 2,404,225. These patents are cited in my U.S. Pat. No. 3,996,620 for "Radiation Shield Apron Construction" wherein the problems inherent in these types of aprons discussed.

The radiation shield apron of my U.S. Pat. No. 3,996,620 overcomes many of the shortcomings of prior aprons of the second type, but, like the others, does not afford the wearer all-around protection from radiation. Such one-piece aprons also tend to restrict rotational movement of the wearer. Also of significance, shield aprons in general are unstylish in appearance, thereby discouraging their use by women.

Normally, greater radiation protection is needed in front of the wearer than in back because the wearer usually faces the radiation source during exposure. However, it is desirable to provide the bodies of those who work near sources of radiation with all-around protection and to allow them free rotational movement. Therefore, a radiation shield garment is needed which provides both greater front protection and all-around protection to the wearer while allowing free rotational movement. There is also a need for such a garment that is attractive to women so as to encourage its use by them.

SUMMARY OF THE INVENTION

The present invention is an improvement in radiation shield garments designed for use by workers exposed to radiation, and particularly female workers. It comprises a two-piece garment, preferably the combination of an adjustably overlapping vest and wraparound skirt. The overlapping portions of each are disposed in front of the body when worn to provide the greatest protection in front, yet all-around protection. The vest and skirt are dimensioned vertically so as to overlap one another when worn to provide continuous vertical as well as all-around protection.

The vest and skirt and each detachably and adjustably closed at their respective overlapping front portions by pairs of complementary adhering closure tabs which adhere to one another when pressed together and extend in horizontal bands, holding the heavy vest and skirt material firmly and snugly around the wearer.

It is a primary object of the present invention to provide an improved radiation shield garment for a worker which provides all-around radiation protection.

A further primary object is to provide a two-piece radiation shield garment which provides continuous vertical and all-around protection.

Another primary object is to provide a two-piece radiation shield garment which is attractively styled as a vest and skirt to encourage its use by women.

Another important object is to provide an improved radiation shield garment affording more radiation protection in front of the worker's body than in back while still providing all-around protection.

Another object is to provide a radiation shield which is adjustable in size.

The foregoing and other objects, features, and advantages of the invention will be more apparent from the following detailed description, which proceeds with reference to the accompanying drawings.

BRIEF DESCRIPTION OF THE DRAWINGS

In the drawings:

FIG. 1 is a front view of the vest portion of the present invention with the vest partially opened;

FIG. 2 is a left side view of the vest of FIG. 1 with such vest closed;

FIG. 3 is a front view of the skirt portion of the present invention with the skirt unwrapped;

FIG. 4 is a front view of the skirt portion of the present invention with the skirt wrapped but partially opened;

FIGS. 5, 6 and 7 are front, left side and rear views, respectively, of the present invention as it appears when worn; and FIG. 8 is an enlarged sectional view taken along the line 8—8 of FIG. 3 showing a typical edge portion of the present invention.

DETAILED DESCRIPTION OF A PREFERRED EMBODIMENT

Referring initially to FIGS. 1 and 2 of the drawing, a vest 10 comprises the upper portion of a two-piece radiation shield garment. It is to be understood, however, that the upper portion may also be a blouse, jacket, or other upper body garment, but the vest is preferred. Such vest includes a rear panel 12 of radiation shielding material which extends continuously vertically from a top shoulder seamline 14 and neckline edge 16 to a generally horizontal bottom edge 18. The rear panel 12 extends horizontally to a generally vertical opposite side seams 20, 21 where it is connected to a pair of overlapping front vest panels 22, 24 of radiation shielding material. A generally vertical side edge of each front panel is connected to a corresponding vertical side edge of the rear shield panel 12 at seams 20, 21, thereby forming the vest. The vest 10 is provided with usual arm openings 26 and neck opening 28.

The rear shield panel 12 and front shield panels 22, 24 are generally of the same vertical length and sufficiently long to extend from the shoulder and neck portion of the body to slightly below waist level when worn as shown in FIGS. 5, 6, and 7 to overlap all around the skirt portion of the garment.

The front shield panels 22 and 24 overlap one another at overlapping areas 30 and 32 when worn. Panels 22 and 24 are adjustably and detachably connected to one another at such overlapping portions by three pairs of complementary adhering closure tabs 34 and 36. Such tabs are sewn or cemented to opposite sides of the front panels and extend in wide horizontal bands. Because of the considerable weight of the vest, it is necessary that enough adhering surface area be provided by the tabs so as to preclude inadvertent opening of the vest induced by such weight. Such closure tabs, when pressed together, interlock and adhere to one another to provide an adjustable and snug fit. Such tabs are known and may be made of tape of the type manufactured by Velcro, S.A. of Switzerland. The closure tabs 34 disposed on the left-hand front shield panel 24 are shown attached to the outside of such front panel, and the mating tabs 36 are shown attached to the inside of right-hand panel 22, although the arrangement could be reversed if an opposite overlap is desired.

When the vest is worn as shown in FIG. 5, overlapping portions 30 and 32 are pressed against one another, thereby engaging the tabs 34 and 36. This allows the vest to be adjustable in size so as to fit snugly to the body and provides rapid and easy donning or removal of the vest. Furthermore, front panels 22 and 24 may be of sufficient width so as to effect a large area of overlap at areas 30 and 32, thus providing double the radiation shielding protection in front of the body than in the back. Phantom lines 35 and 37 in FIG. 1 show a greater area of overlap due to greater width of front panels 22 and 24 or due to a smaller-sized person wearing the vest. Regions, 30, 32 forming the overlapping area of the vest, when worn, are also referred to herebelow as vest outer portions, with the remaining, nonoverlapping area of the vest, also being referred to herebelow as the vest central portion. The band areas of the tabs must be sufficient to resist the tendency of the front panels to pull open under their own weight and must be of sufficient horizontal extent to provide the desired size adjustment.

In FIGS. 3 and 4, the skirt portion 38 of the garment is shown. The skirt is of wraparound style, shown unwrapped in FIG. 3 and wrapped in FIG. 4. The lower garment portion may also comprise pants or other lower body garment, but the skirt is preferred. The skirt is constructed of a rear skirt panel 40 of radiation shielding material and left and right front skirt panels 42 and 44, also of radiation shielding material. The front skirt panels are connected one to each of opposite side edges of the rear skirt panel along generally vertical seams 46, 48, thereby forming the wraparound skirt. The rear skirt panel 40 and front skirt panels 42 and 44 are generally of the same length so as to extend from a hemline 49 near the knee area of the body to an upper waist band 50. However, such skirt may be of any desirable and stylish length, preferably covering at least the upper leg and abdominal areas. Waist band 50 is disposed beneath the overlapping lower edge portion of the vest when worn, as shown by dashed lines in FIGS. 5 and 7.

The front skirt panels 42 and 44 are provided as shown with a pair of complementary adhering closure tabs 52 and 54 of the same type as tabs 34 and 36 on the vest 10. Closure tab 54 is shown in dashed lines in FIG. 3 to indicate that it is disposed on the reverse side of panel 42. Additional pairs of such tabs may be used if desired. The tabs 52, 54 extend in long horizontal overlapping bands completely across the overlapping front panels 42 and 44 to preclude inadvertent opening of the skirt due to its considerable weight, and to provide ample size adjustment.

The skirt is wrapped around the body and folded over such that closure tabs 52 and 54 engage one another in front of the body as shown in FIGS. 4 and 5. This construction allows the wearer to adjust the size fitting of the skirt such that it fits snugly about the waist and hip area of the body to distribute its weight over a wide area.

The front panels 42 and 44 may be of sufficient width and shape so as to enable each to extend substantially completely across the front of the lower body as shown, thereby affording double the radiation shielding protection in the front of the body than in the back. This feature is shown in FIGS. 5 and 7 wherein the opposite vertical side edges 46 and 48 of the skirt lie in a generally vertical line along the opposite sides of the body with the overlapping front panels 42 and 44 disposed across the front of the body. Regions forming the overlapping area of the skirt, when worn, are also referred herebelow as skirt outer portions, with the remaining, nonoverlapping area of the skirt, also being referred to herebelow as the skirt central portion.

As also shown in FIGS. 5–7, the two-piece radiation shield garment provides continuous vertical and all-around protection to the wearer while providing greater radiation protection in front than in back. Twisting movement of the wearer is enhanced because the upper and lower portions of the garment are separate and unconnected. In addition, the garment may be stylishly shaped and decorated to be an attractive garment encouraging its use by women workers.

Referring now to FIG. 8, a typical edge portion 56 is shown, such as at edge 18 of the vest or hemline 49 of the skirt. Binding tape 58 encloses front and back cover sheets 60 and 62 of a nonshielding fabric or material such as vinyl or some other suitable nonshielding fabric. Multiple inner layers or sheets of radiation shielding material 64, 66, 68, 70, 72 are coextensive with and sandwiched between the cover sheets and double stitched with appropriate thread as shown at 74. It is to be understood that any number of layers of radiation shielding material may be utilized depending on the amount of protection desired. The vertical side seams 20 and 21 of the vest and 46 and 48 of the skirt may be constructed of two edge seams of the type shown in FIG. 8 sewn together in an overlapping fashion (not shown).

The inner layers 64 through 72 typically comprise multiple layers of flexible lead sheeting as described in my U.S. Pat. No. 3,996,620. The composition of such sheets is disclosed in numerous prior patents, including U.S. Pat. Nos. 2,404,225; 3,093,829; 2,858,451; 2,052,788; and 3,514,607. Such layers account for the considerable weight of the garment. The cover sheets 60 and 62 may have an attractively designed color print on their outer surfaces to enhance the attractiveness of the shield and encourage its use.

The radiation shield is constructed for attractiveness and size adjustment while providing free twisting movement of the wearer and all-around radiation protection. The Velcro-type closure bands ensure rapid and easy detachable closure for the skirt and vest allowing each to be adjustable so that they may be worn snugly during use thereby distributing their weight over the body providing maximum comfort and minimum fatigue.

Adhering closure tabs 52 and 54 overlap in front of the body so that the upper waist band portion 50 is at least at waist level or higher. The vest is then slipped on as any vest, and overlapping portions 30 and 32 are connected by complementary closure tabs 34 and 36 such that the vest fits snugly and has the lower edges of front panels 20 and 24 and the bottom edge 18 vertically overlapping the upper waist band portion 50 of the skirt.

Having illustrated and described the principles of my invention by what is presently a preferred embodiment thereof, it should be apparent to persons skilled in the art that such embodiment may be modified in arrangement, detail and composition without departing from such principles. I claim as my invention all embodiments and modifications coming within the true spirit and scope of the accompanying claims.

I claim:

1. A radiation shield garment for shielding the human body from radiation comprising in combination:
   a vest for shielding the upper body and a skirt for shielding the lower body;
   said vest including, when worn, overlapping front panel portions covering a front portion of the upper body and a rear panel portion forming a continuation of the front panel portions covering a back portion of the upper body, said front and rear panel portions including at least one layer of flexible radiation shielding material substantially coextensive with such portions so as to provide all-around radiation protection to the upper body from the waist area to the shoulder and neckline area of said upper body;
   said skirt including, when worn, overlapping front skirt panel portions covering a front portion of the lower body and a rear skirt panel portion forming a continuation of the front panel portions covering the back portion of said lower body, said front and rear skirt panel portions including at least one layer of flexible radiation shielding material substantially coextensive with said portions so as to provide all-around radiation protection to the lower body from the waist area downwardly over at least the upper leg area of said lower body;
   said vest and skirt each including closure means to adjustably secure their respective front panel portions in overlapping relationship;
   said vest and skirt being dimensioned vertically so as to overlap one another when worn, thereby together providing vertically continuous radiation protection to the body.

2. A radiation shield garment according to claim 1 wherein said vest and skirt are constructed of nonshielding fabric material covers covering a plurality of layers of flexible inner sheets of radiation shielding material, said nonshielding covers being coextensive with said inner sheets.

3. A radiation shield garment according to claim 1 wherein said overlapping front panel portions of said vest and skirt are detachably and adjustably connected to one another respectively by at least one pair of complementary adhering closure tabs providing adjustable closure and size fitting of said vest and skirt.

4. A radiation shield garment according to claim 1 wherein said rear skirt panel portion of said skirt comprises a single large panel and said front skirt panel portions comprise a pair of smaller panels of substantially equal length to said large panel, each said smaller panel connected to said large panel at an opposite peripheral side edge of said large panel, thereby being separated by such single large panel and forming an adjustably overlapping wraparound skirt.

5. A radiation shield garment according to claim 1 wherein said closure means of said vest comprises a plurality of vertically spaced pairs of complementary adhering closure tabs extending in horizontal bands across said overlapping front panel portions so as to provide adjustable closure of said vest and resist opening of said panel portions induced by the weight of said vest.

6. In a radiation shield garment, a vest comprising:
   a rear panel covering the back of the upper body extending continuously vertically from the top of the shoulder line and neckline of said body downwardly to at least body waist level and having generally vertical opposite side edges;
   a pair of overlapping front panels for covering the front of said upper body, each said front panel connected to one of said opposite side edges of said rear panel and extending continuously vertically from said top shoulder line and neckline to at least body waist level;
   said rear and front panels being constructed of nonshielding fabric material covers covering a plurality of layers of flexible inner sheets of radiation shielding material;
   and said overlapping front panels being detachably and adjustably connected to one another by at least one pair of complementary adhering closure tabs providing adjustable closure and size fitting of said vest.

7. In a radiation shield garment, a skirt comprising:
   a rear skirt panel for covering the rear of the lower body extending continuously vertically from the waistline downwardly over at least the upper leg area of said lower body and having a pair of generally vertical opposite side edges;
   a pair of overlapping front skirt panels for covering the front of said lower body of substantially equal length to said rear panel, each said front skirt panel connected to one of said opposite side edges of said rear panel, thereby forming an overlapping wraparound skirt;
   said rear and front skirt panels being constructed of nonshielding fabric material covers covering a plurality of layers of flexible inner sheets of radiation shielding material providing a flexible shielding material;
   and said overlapping front panels detachably and adjustably connected to one another by at least one pair of complementary adhering closure tabs thereby providing adjustable closure and size fitting of said skirt.

8. A radiation shield garment according to claim 7 wherein said closure tabs of said skirt extend in horizontal bands across said overlapping front skirt panels so as to provide adjustable closure of said skirt and to resist opening of said overlapping panel portions induced by the weight of said skirt.

9. A radiation shield garment for shielding the human body from radiation comprising in combination:
   a vest for shielding an upper body region extending from the waist area through the shoulder and neckline area and a skirt for shielding a lower body region extending from the waist area downwardly over at least the upper leg area;
   said vest including, when worn, overlapping vest outer portions covering a portion of the upper body region and a vest central portion forming a continuation of said vest outer portions and covering remainder portions of the upper body region, said vest outer and central portions including at least one layer of flexible radiation shielding material so as to provide all-around radiation protection to the upper body regions;

said skirt including, when worn, overlapping skirt outer portions covering a portion of the lower body region and a skirt central portion forming a continuation of said skirt outer portions covering remainder portions of the lower body region, said skirt outer and central portions including at least one layer of flexible radiation shielding material so as to provide all-around radiation protection to such lower body regions;

said vest and skirt each including closure means associated with said vest and skirt outer portions, respectively, to adjustably secure their respective outer portions in overlapping relationship;

said vest and skirt being dimensioned vertically so as to overlap one another when worn, thereby together providing vertically continuous radiation protection to the body.

* * * * *